United States Patent
Cocchi et al.

(10) Patent No.: US 9,756,870 B2
(45) Date of Patent: Sep. 12, 2017

(54) DEVICE FOR DETECTING THE BACTERIAL CHARGE IN A LIQUID OR SEMI-LIQUID FOOD PRODUCT

(75) Inventors: Andrea Cocchi, Calderara di Reno (IT); Roberto Lazzarini, Reggio Emilia (IT)

(73) Assignee: ALI S.p.A.-CARPIGIANI GROUP, Bologna (IT)

( * ) Notice: Subject to any disclaimer, the term of this patent is extended or adjusted under 35 U.S.C. 154(b) by 80 days.

(21) Appl. No.: 13/046,401

(22) Filed: Mar. 11, 2011

(65) Prior Publication Data

US 2011/0256617 A1 Oct. 20, 2011

(30) Foreign Application Priority Data

Apr. 15, 2010 (IT) ................ BO2010A0233

(51) Int. Cl.
C12M 1/34 (2006.01)
A23G 9/22 (2006.01)
G01N 33/487 (2006.01)

(52) U.S. Cl.
CPC ....... *A23G 9/228* (2013.01); *G01N 33/48735* (2013.01)

(58) Field of Classification Search
CPC ........ G01N 27/02; A23G 9/228; A23G 9/281; A23G 9/30; A23G 9/305; A23C 7/02; A23L 3/001; A23V 2300/00
(Continued)

(56) References Cited

U.S. PATENT DOCUMENTS 3,519,549 A * 7/1970 Grassmann et al. .......... 204/600
4,758,097 A 7/1988 Iles, Sr.
(Continued)

FOREIGN PATENT DOCUMENTS

CN 1035090 8/1989
CN 1182545 5/1998
(Continued)

OTHER PUBLICATIONS

Shi K et al: "Time Evolution of Double-Diffusive Convection in a Vertical Cylinder With Radial Temperature and Axial Solutal Gradients", International Journal of Heat and Mass Transfer, Pergamon Press, GB, vol. 49, No. 5-6, Mar. 1, 2006, pp. 995-1003, XP025238589, ISSN: 0017-9310, DOI: 10.1016/J.IJHEATMASSTRANSFER.2005.09.009.
(Continued)

*Primary Examiner* — William H Beisner
*Assistant Examiner* — Danielle Henkel
(74) *Attorney, Agent, or Firm* — Shuttleworth & Ingersoll, PLC; Timothy Klima

(57) ABSTRACT

A device (1) for detecting the bacterial charge in a liquid or semi-liquid food product comprises a main containment body (2), an analysis chamber (3), located inside the containment body (2) and designed to contain a certain quantity of product to be examined, one or more heating means (4) designed to heat the product inside the analysis chamber (3), at least one temperature sensor (5) designed to monitor the temperature of the product inside the analysis chamber (3) and sensor means (6) designed to detect the impedance in the product inside the analysis chamber (3). The analysis chamber (3) has an elongate shape and extends along a principal axis (3a), while the one or more heating means (4) are symmetrical about a plane at right angles to the principal axis (3a).

23 Claims, 7 Drawing Sheets

(58) Field of Classification Search
USPC .......................................... 435/286.1, 287.1
See application file for complete search history.

(56) References Cited

U.S. PATENT DOCUMENTS

| | | | |
|---|---|---|---|
| 5,069,364 A | 12/1991 | McGill | |
| 5,133,937 A * | 7/1992 | Frackleton et al. | 422/81 |
| 5,229,150 A | 7/1993 | Ahnell et al. | |
| 5,349,825 A | 9/1994 | Duke et al. | |
| 5,463,878 A | 11/1995 | Parekh et al. | |
| 5,473,909 A | 12/1995 | Kateman et al. | |
| 5,718,816 A * | 2/1998 | Savage | G01N 33/4915 204/400 |
| 6,006,535 A | 12/1999 | Cathenaut | |
| 7,681,761 B2 | 3/2010 | Harra | |
| 8,479,531 B2 | 7/2013 | Maeda et al. | |
| 2003/0102854 A1* | 6/2003 | Gascoyne et al. | 324/71.4 |
| 2003/0157587 A1* | 8/2003 | Gomez | G01N 33/56911 435/30 |
| 2004/0219269 A1 | 11/2004 | Cathenaut et al. | |
| 2007/0102448 A1 | 5/2007 | Harra | |
| 2007/0251260 A1 | 11/2007 | Baxter et al. | |
| 2008/0034839 A1* | 2/2008 | Ante | G01N 1/2205 73/23.31 |
| 2008/0073376 A1 | 3/2008 | Gist et al. | |
| 2008/0226779 A1* | 9/2008 | Cocchi et al. | 426/231 |

FOREIGN PATENT DOCUMENTS

| | | |
|---|---|---|
| CN | 1668508 | 9/2005 |
| CN | 1780785 | 5/2006 |
| CN | 101252858 | 8/2008 |
| EP | 0448503 | 9/1991 |
| EP | 1716760 | 11/2006 |
| EP | 1972198 | 9/2008 |
| EP | 2098729 | 9/2009 |

OTHER PUBLICATIONS

Italian Search Report dated Nov. 17, 2010 from counterpart application.
Italian Search Report dated Dec. 15, 2011 from counterpart foreign application BO20110165-20545-0686.
Chinese Office Action dated Jun. 5, 2014 from counterpart application No. 21210164202.0 20545-0688.

* cited by examiner

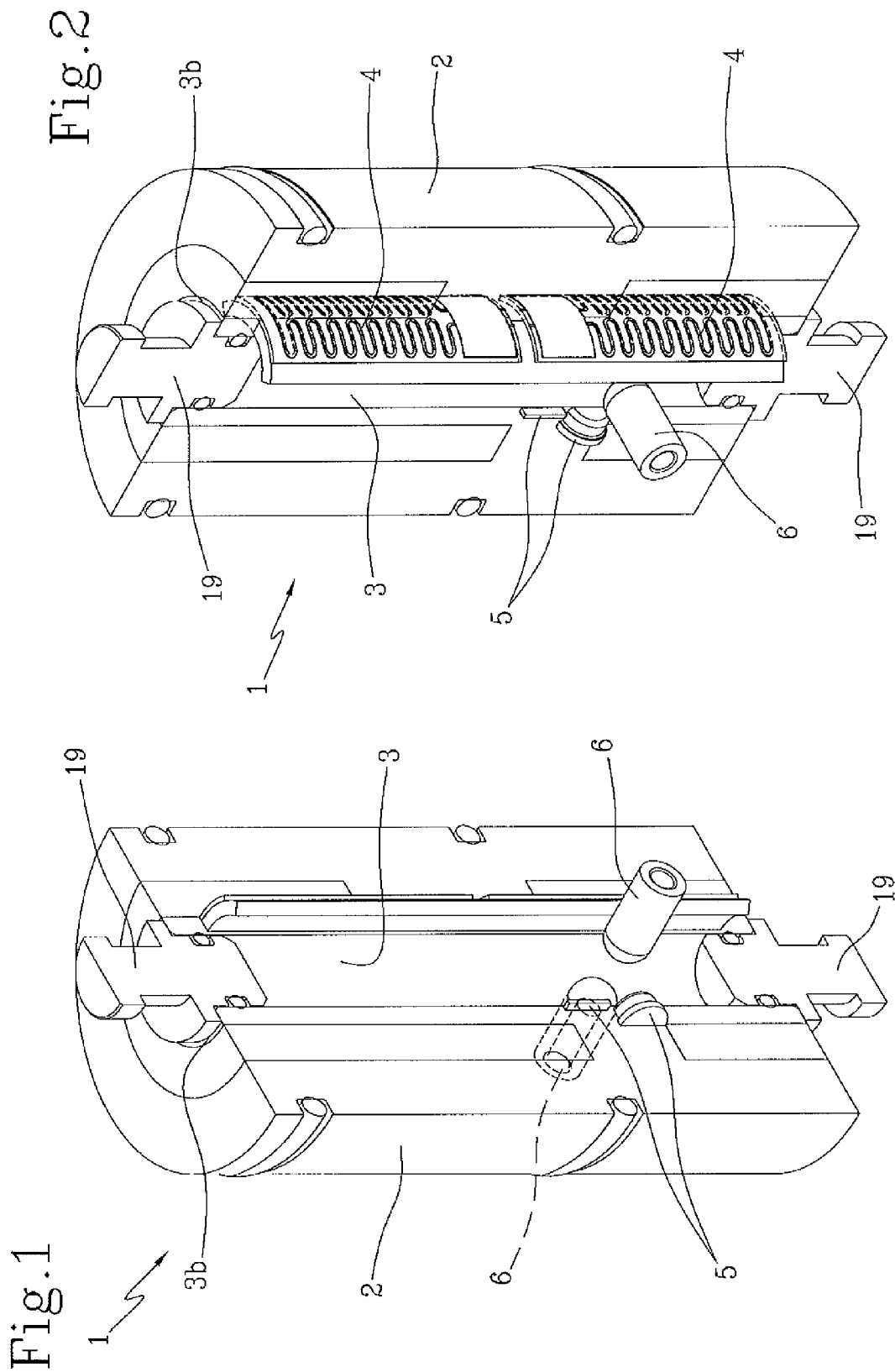

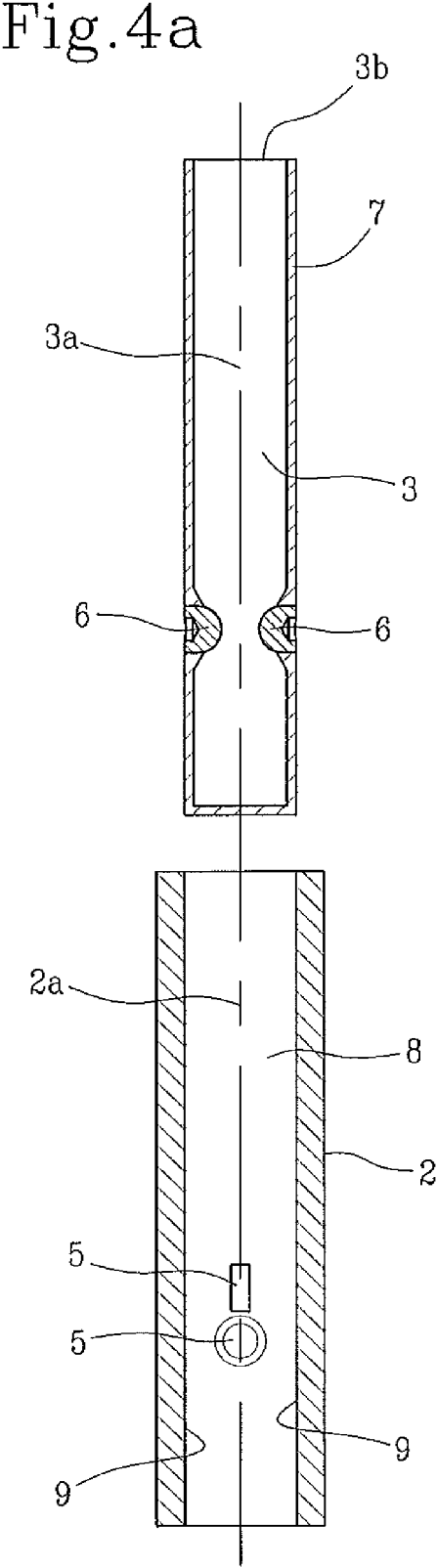
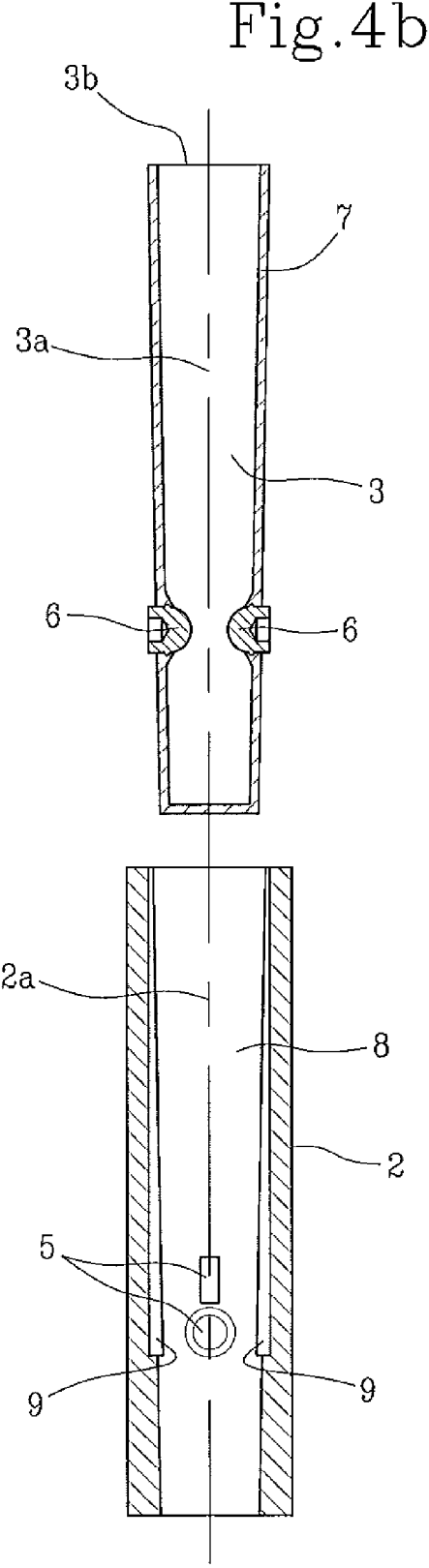

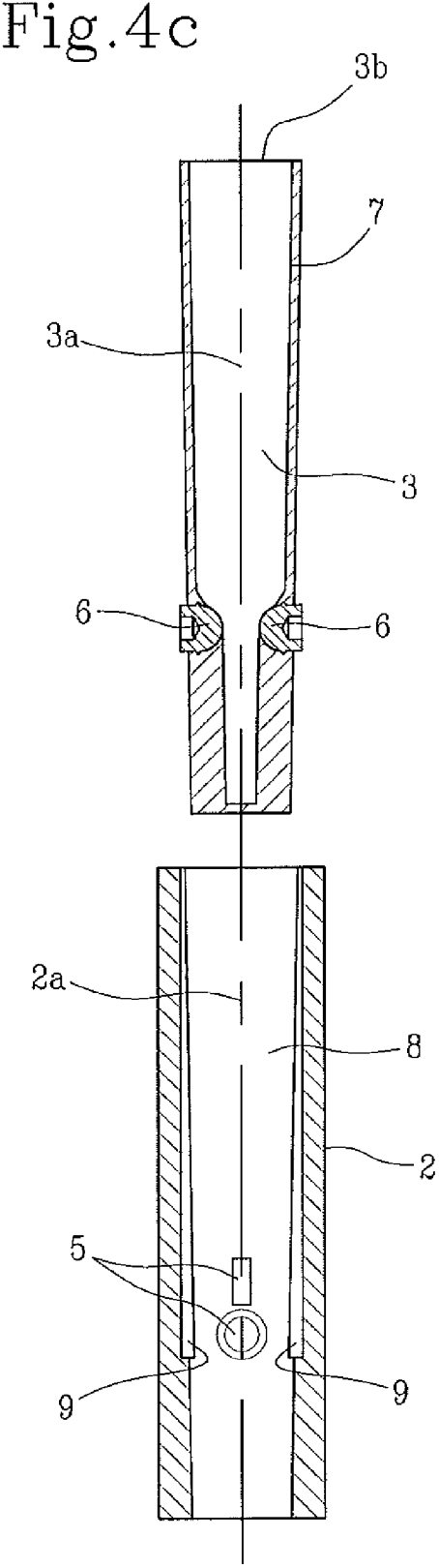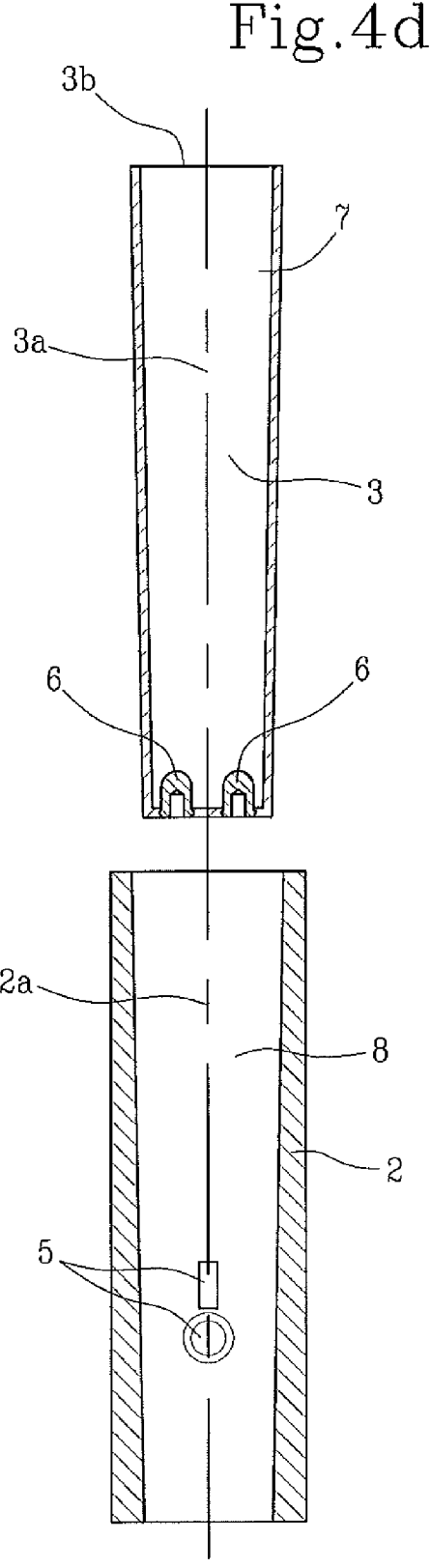

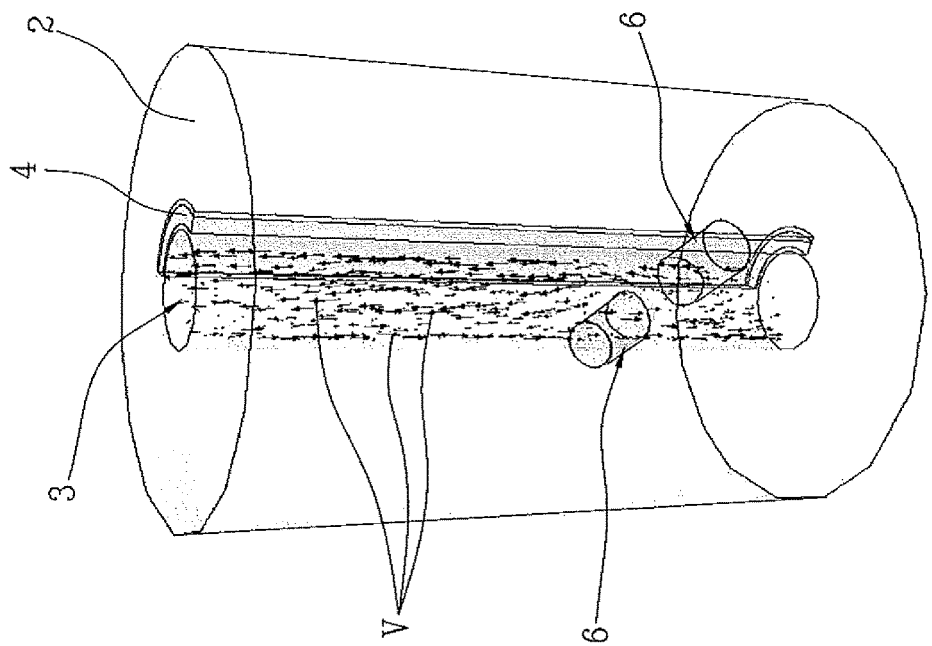
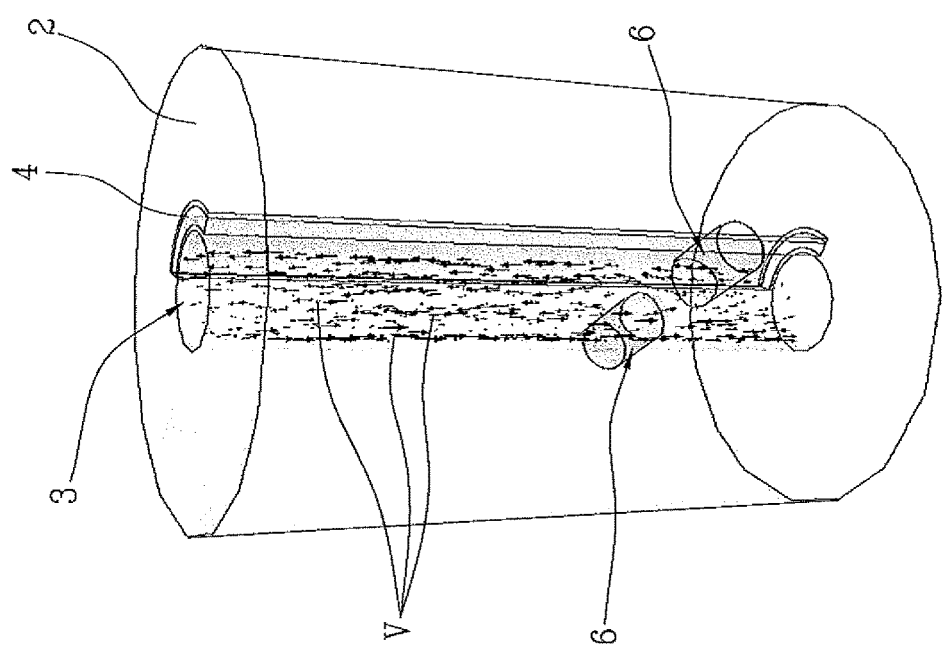

DEVICE FOR DETECTING THE BACTERIAL CHARGE IN A LIQUID OR SEMI-LIQUID FOOD PRODUCT

This application claims priority to Italian Patent Application BO2010A000233 filed Apr. 15, 2010, the entirety of which is incorporated by reference herein.

BACKGROUND OF THE INVENTION

This invention relates to a device for detecting the bacterial charge in a liquid or semi-liquid food product.

More specifically, the invention can be used in plant or machinery for the dairy industry and, more generally, in processing plant for the food industry.

The invention also relates to a machine for making and dispensing liquid and semi-liquid food products.

More specifically, but without limiting the scope of the invention, the machines referred to herein are machines for making and dispensing granitas, sorbets or slush drinks, ice creams, soft ice creams, whipped cream, yogurt and the like, as well as machines for making and storing mixes for ice cream, creams, sauces, soups, food mixes in general and the like.

As is known, machines of the above mentioned kind comprise a container for the basic product, consisting for example of whipping cream, ice cream product mixes, syrups and the like, and a feed circuit which is provided with devices such as refrigerating means for processing the basic product and at the end of which there are dispensing devices such as nozzles or taps adapted to deliver the finished product (whipped cream, ice cream, granita, etc.).

These machines, also considering the fact that the products they process are highly perishable, are subject to frequent checks and maintenance in order to guarantee optimum hygiene conditions along the entire feed circuit.

The main problem connected with the use of these machines for professional purposes is due to the presence of milk-based mixtures and the consequent need to clean and sanitize the machines in order to prevent the proliferation of germs and bacteria.

At present, a preventive maintenance procedure is carried out at specified intervals, from daily to twice-weekly, depending on machine characteristics. For example, machines without built-in heat treatment systems must be sanitized at least once every seventy-two hours, while self-pasteurizing machines are sanitized fortnightly.

In this regard, European patent application EP1716760, in the name of the same Applicant as this invention, discloses a machine for producing and dispensing liquid or semi-liquid consumer food products which is equipped with a washing device used to introduce, in alternate steps, into the feed and treatment circuit a flow of fluid in the liquid or vaporized state to allow the circuit to be washed and sanitized. A central processing unit controls and regulates the steps in the washing and sanitizing procedure.

Whether a machine must be disassembled for cleaning or is equipped with a built-in automatic sanitizing system, all the sanitizing operations are preventive and cannot guarantee conditions of total hygiene.

Although methods for estimating the cell mass of a bacterial population exist, these methods involve laboratory tests, high costs and extended times and are used, for example in the dairy industry, only in random testing.

To overcome these drawbacks, the Applicant has devised a machine for making and dispensing liquid or semi-liquid food products which is equipped with a device for checking the bacterial charge in both the basic and the finished product.

This device can determine the bacterial charge of the food product at any point on the machine.

The device, however, has some disadvantages connected with the precision of the measurements obtained. In effect, convective motions in the product inside the device upset and negatively affect measurement.

SUMMARY OF THE INVENTION

The aim of this invention is therefore to provide a device for detecting the bacterial charge in a liquid or semi-liquid food product and which overcomes the disadvantages of the prior art.

In particular, the aim of the invention is to provide a detecting device that is capable of accurately assessing the bacterial charge in a liquid or semi-liquid food product without its measurement being negatively affected by convective motions produced in the fluid by temperature variations.

Another aim of the invention is to provide a machine for making and dispensing liquid and semi-liquid food products which is equipped with such a device.

Lastly, this invention has for an aim to provide a portable kit for detecting and analyzing the bacterial charge in a liquid or semi-liquid food product.

BRIEF DESCRIPTION OF THE DRAWINGS

The technical features of the invention, with reference to the above aims, are clearly described in the claims below and its advantages are more apparent from the detailed description which follows, with reference to the accompanying drawings which illustrate a preferred, non-limiting example embodiment of the invention and in which:

FIGS. 1 and 2 show the two halves of the device of this invention cross-sectioned along a vertical plane through the vertical axis of symmetry;

FIGS. 4a-4d are cross sections illustrating different variants of a part of the device of the invention;

FIGS. 6a-6d illustrate the distribution of product motion at different moments in time in the analysis chamber of the device of this invention.

DESCRIPTION OF THE PREFERRED EMBODIMENTS

Figure 3:
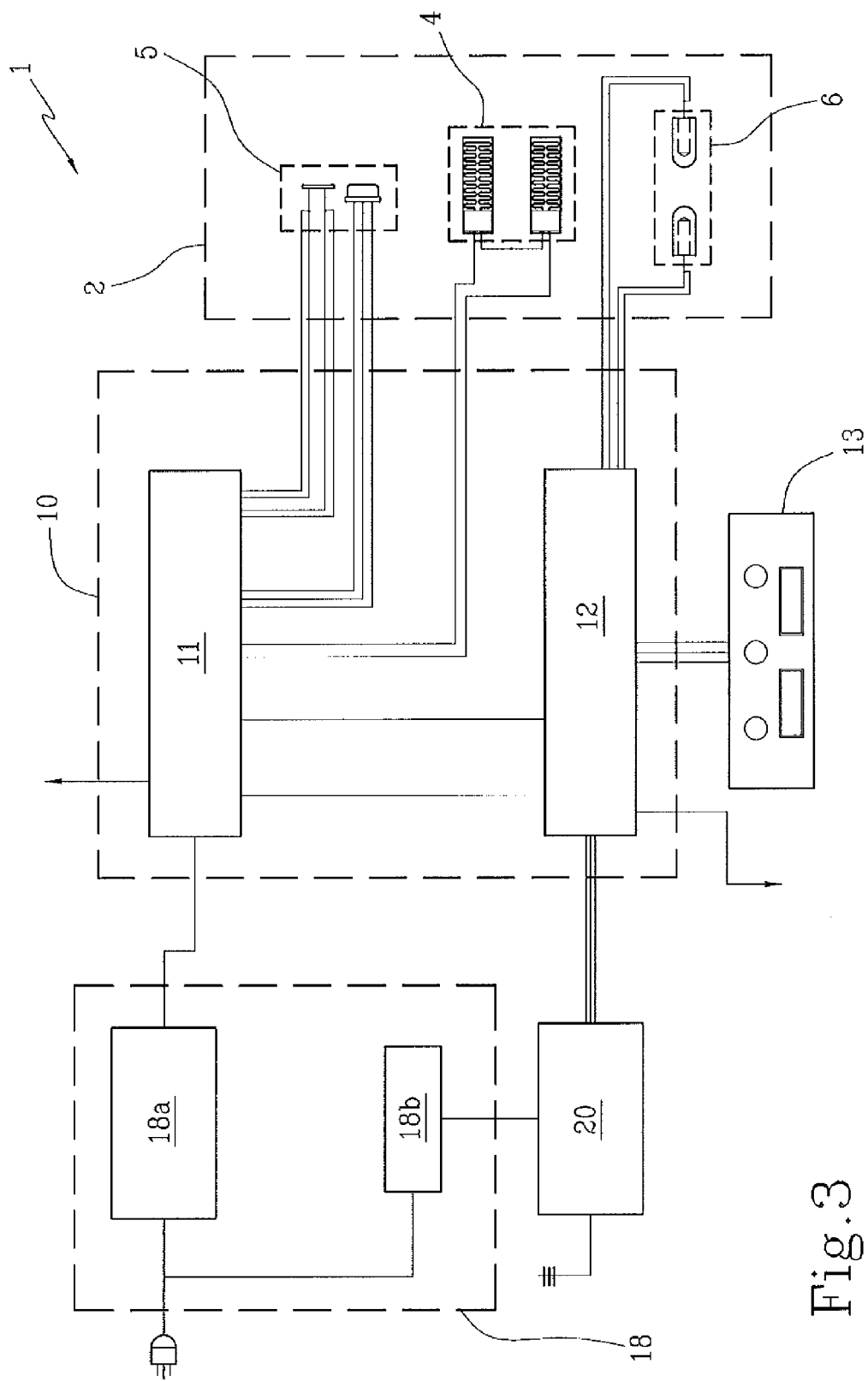
FIG. 3 is a block diagram schematically illustrating the operation of the device of this invention.
Figure 5:
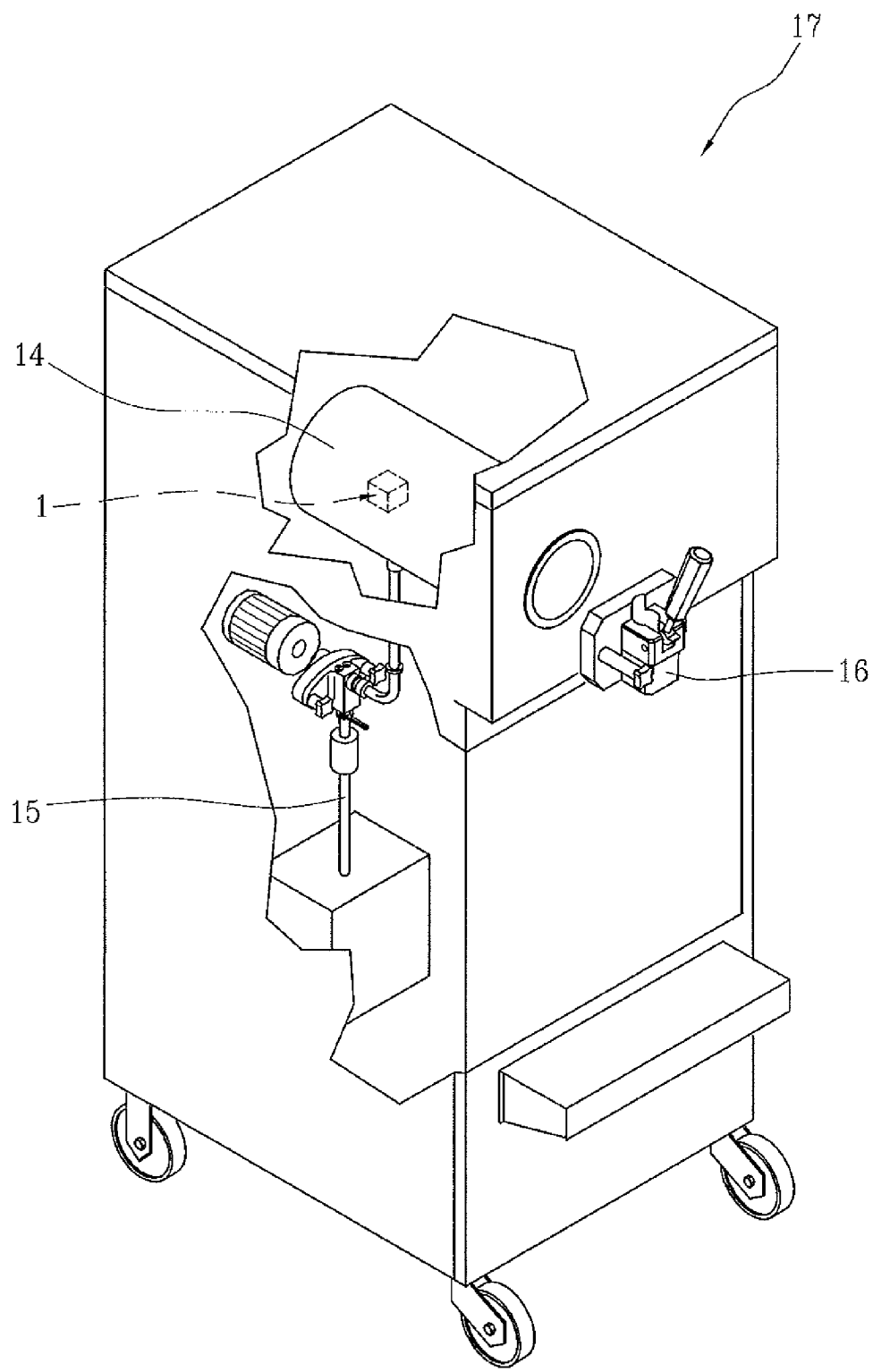
FIG. 5 is a perspective view, with some parts cut away and others in dashed line style, illustrating a machine for making and dispensing liquid and semi-liquid food products which is equipped with a device for detecting the bacterial charge.

With reference to FIGS. 1 and 2, the numeral 1 denotes in its entirety a device for detecting the bacterial charge in a liquid or semi-liquid food product.

The device 1 comprises a main containment body 2, preferably cylindrical in shape.

Inside the body 2 there is an analysis chamber 3 designed to contain a certain quantity of product to be analyzed.

By analysis chamber 3 is meant the compartment where the bacterial test is performed.

The device 1 also comprises one or more heating means 4, designed to vary the temperature inside the analysis chamber 3, and more precisely, to heat the product to be tested, inside the analysis chamber 3, to a preset value.

In one embodiment, the heating means 4 are positioned at least partly around the analysis chamber 3. As illustrated schematically in FIG. 2, the heating means 4 are positioned outside the analysis chamber 3.

It will be understood that in slightly different embodiments, the heating means 4 may also be positioned inside the analysis chamber 3.

The device 1 also comprises at least one temperature sensor 5, located advantageously in the side wall of the containment body 2 and facing the inside of the analysis chamber 3.

The temperature sensor 5 monitors the temperature of the product inside the analysis chamber 3.

Also provided are sensor means 6 designed to promote the circulation of electric current in the analysis chamber 3 and to measure the impedance in the product to be tested.

More specifically, the sensor means 6 are preferably a pair of electrodes, mounted symmetrically about an axis of symmetry 2a of the containment body 2 and protruding partly into the analysis chamber 3.

In other words, the electrodes place the inside of the analysis chamber 3 in electrical communication with the outside of it.

They may be mounted at right angles to the axis of symmetry 3a, thus lying along the side wall of the chamber 3, or parallel to the axis of symmetry 3a, thus lying on the base wall, that is the bottom wall, of the chamber 3.

The electrodes 6 consist preferably of two rounded steel cylinders with hemispherical profile on the side that is immersed in the product to be tested, that is, on the side facing the analysis chamber 3; and with threading on the opposite side, for connection to the measurement cables. Their function is to cause the set current to flow in the product.

Advantageously, the analysis chamber 3 has en elongate shape and extends along a principal axis 3a that coincides with the axis of symmetry 2a of the containment body 2.

In an alternative embodiment, the analysis chamber 3 is removably associated with the containment body 2.

In other words, the analysis chamber 3 is contained inside a disposable cartridge 7 to be substituted after each time the product is analyzed.

The cartridge may be cylindrical, that is to say, having a constant outside diameter (FIG. 4a), or tapered towards the bottom (FIGS. 4b-4d), that is to say, having e an outside diameter that decreases towards the bottom, thus advantageously allowing extraction of the male component in the case of injection molding.

In both the fixed and the removable configuration, the analysis chamber 3 preferably has a circular inside cross section whose diameter is constant or variable along the axis 3a. The circular cross section allows the product to be uniformly distributed in the chamber, without accumulating in some parts more than others, and since there are no corners, also makes it easier to clean the chamber 3 between one analysis and another.

Advantageously, the ratio between the height and the inside diameter of the analysis chamber 3 is greater than or equal to 2. With reference to a configuration of the analysis chamber 3 where the circular cross section, and hence the diameter, varies along the axis, the diameter referred to here is the largest diameter.

FIGS. 4a-4d show some embodiments of the chamber and, more specifically, the images show different, alternative embodiments of the chamber in the removable form. The configurations illustrated, however, might also apply to the chamber in the fixed form.

These drawings, which are cross sections of the analysis chamber 3, show the internal geometry of the chamber 3 which may be, for example, cylindrical, frustoconical or funnel-shaped.

As shown in FIGS. 4a-4d, even in the case of a removable analysis chamber 3, the electrodes 6 face the inside of the chamber 3.

More specifically, the analysis chamber 3 comprises a pair of electrodes embedded in the wall of the cartridge 7 and facing both the inside and the outside of the analysis chamber 3 in order to electrically connect the inside of the analysis chamber 3 with the outside.

In FIGS. 4a-4c, the electrodes are positioned at right angles to the axis of symmetry 3a, and are thus positioned in the side wall of the cartridge 7, whilst in FIG. 4d, the electrodes are parallel to the axis of symmetry 3a since they are positioned in the base wall of the cartridge 7.

In the configuration with removable analysis chamber 3, the containment body 2 has a housing 8 into which the cartridge 7 containing the chamber 3 is inserted.

Internally, the containment body 2 has at least two sliding contacts 9 which can be associated with the electrodes of the analysis chamber 3.

The analysis chamber 3 is delimited laterally and has at least one openable end 3b.

If necessary, that end can be closed by a closing element 19 during analysis.

The product might therefore be fed in and extracted from a single end, after being analyzed, or it might be fed in through one end, left to stand in the analysis chamber 3 while it is analyzed, and then expelled through the opposite end.

The heating means 4 are positioned symmetrically about an orthogonal plane at right angles to the principal axis 3a of the analysis chamber 3. The heating means are advantageously positioned around the side wall of the analysis chamber 3 and only along one surface portion, thereby creating a chamber portion with a "warm" wall and a chamber portion with a "cool" wall, so as to produce convective motions in the product.

Preferably, the heating means comprise a pair of resistors, positioned symmetrically about the orthogonal plane; more specifically, the heating means 4 may comprise a thin, rounded copper plate on which the two resistors are glued. In this case, the resistors may be adhesive and flexible.

During the analysis procedure, the device 1 or, more specifically, the containment body 2 and the analysis chamber 3, must be positioned in such a way that the principal axis 3a, or axis of symmetry, is vertical.

This, combined with the specific arrangement of the heating means, makes it possible to prevent the convective motions which are produced within the product from negatively affecting the result of bacterial charge measurement.

The main containment body 2 is electrically connected to an electronic controller unit 10 which controls and coordinates the temperature sensor 5, the sensor means 6 and the heating means 4.

More specifically, the electronic controller unit 10 receives as input the values of the temperature inside the analysis chamber 3, measured by the temperature sensor 5, and interacts with the heating means 4 to control and vary the temperature according to the desired values.

Further, the electronic controller unit 10 is operatively connected to the sensor means 6, and thus to the electrodes 6, for measuring the impedance inside the product from which capacitance can be derived in order to determine the bacterial charge.

Preferably, the electronic controller unit 10 comprises a temperature regulator 11, connected to the temperature sensor 5 and to the heating means 4, and an electronic card 12 connected to the sensor means 6 and to the same temperature regulator 11.

The temperature regulator 11 checks the resistors based on the temperature measured by the sensor 5 in order to keep the fluid product inside the analysis chamber 3 at a temperature, constant over time and equal to the set temperature.

The communication between the temperature regulator 11 and the electronic card 12 may be unidirectional or bidirectional.

Lastly, a control panel 13 makes it possible to interact with the electronic controller unit 10 to enter the desired parameters and/or read out the values resulting from analysis.

The control panel 13 may comprise, for example, an LCD display, possibly but not necessarily, of the touch screen type, or visual LED control signals. There are also data setting or selector pushbuttons, and/or other technically equivalent elements for interacting with the electronic controller unit 10.

All of the above are electrically powered by a power supply unit 18, which preferably comprises a transformer 18a and a power pack 18b which preferably delivers a voltage of 12 Vdc.

Advantageously, a modem 20, for example of the GPRS type, is provided for transmitting/receiving the data processed by the electronic card 12.

During measurement to determine bacteria concentration, the product sample is incubated inside the analysis chamber 3 at a temperature that promotes the growth of the bacteria in the product (35° C. in the case of ice cream mixes) and samples of the impedance across the two electrodes 6 immersed in the product are taken by the electronic controller unit 10: capacitance values are derived from the impedance and by analyzing these over time, it is possible to determine the bacteria concentration initially present in the product being tested.

When measuring the electrical characteristics of the product, special attention must be paid to the temperature of the sample: the electrical characteristics of the product depend to a large extent on the temperature and thus, even the smallest variations produce large variations in the impedance measurements, which can have a negative effect on the measurement.

FIGS. 6a-6d show the distribution of motion in the fluid (indicated by vectors V) inside the analysis chamber 3 at different moments during the measurement of the bacterial charge in the product. The special arrangement of the heating means makes it possible to obtain a pattern where motion is ascending near the warm wall and descending near the cool wall.

Figure 6B:
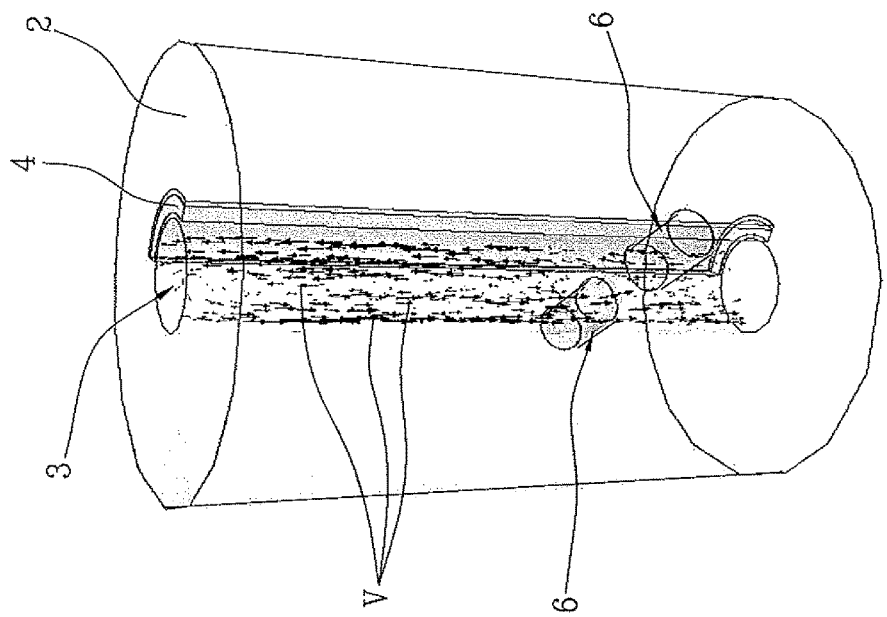
Figure 6A:
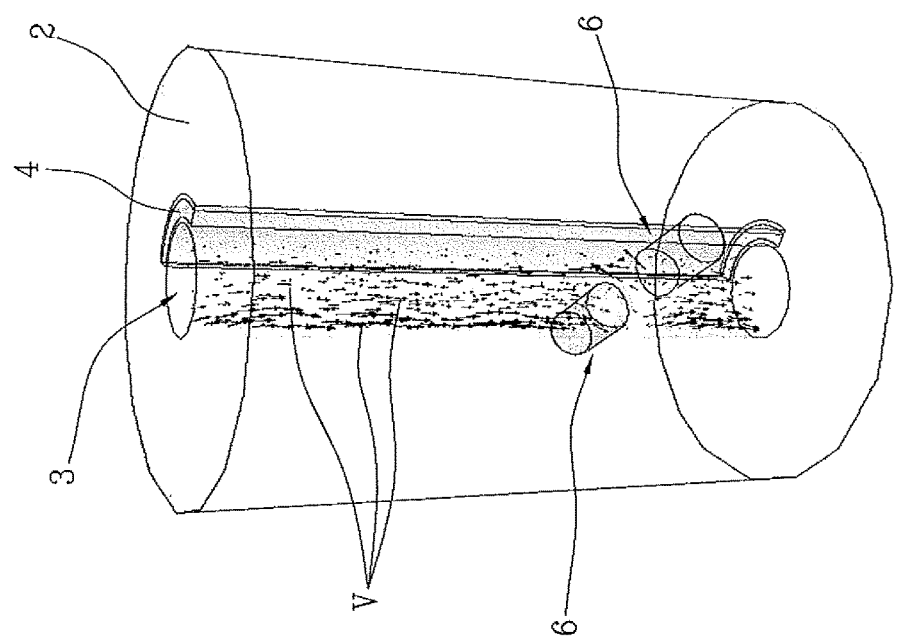

An initial stage of irregular motions occurs in the first 60 seconds approximately (FIG. 6a), after which the motion is stabilized and reaches the maximum speed peak after approximately 6 minutes (FIG. 6b).

Then, thanks to the redistribution of the temperature in the fluid, the convective motions are stabilized (FIG. 6c) until their values are mostly constant. The maximum steady-state speed is registered in the proximity of the warm wall, in the upper zone of the analysis chamber 3. In the zone between the electrodes, on the other hand, the speed is low, being approximately one third of the maximum speed.

Thus, under steady-state conditions, in the zone between the electrodes, that is, the zone where the impedance of the fluid is measured, the average speed registered varies between 0.05 and 0.09 m/s (FIG. 6d).

The motion in this zone is extremely reduced and thus the speed of the fluid in that zone does not in any way affect the measurement of the bacterial charge, allowing precise and reliable results to be obtained.

The device may be installed in a machine 17 for producing and dispensing liquid or semi-liquid food products, comprising a food product container 14, a food product feeding and treating circuit 15, dispensing means 16 located at an outlet end of the feeding and treating circuit 15.

The device may be mounted at different points in the machine, depending on the zone to be monitored, so as to provide a constant, real-time indication of the actual bacterial charge in the product being dispensed.

Thus, the device 1 may be installed, for example, along the feed and treatment circuit 15, or inside the mix and freeze chamber 14, or upstream of the pasteurizing device or along a secondary line feeding out of the finished product container, or inside the door, or at any of several other locations inside or outside the machine 17.

To be able to use the device even with machines for producing and dispensing liquid or semi-liquid food products currently on the market and hence not equipped with a device of this kind, the Applicant has devised a portable kit comprising a transportable enclosure, such as a carrying case, for example, containing the detection device 1 according to the invention.

The carrying case therefore includes the main containment body that accommodates the analysis chamber, the electronic controller unit 10 and a power pack, preferably battery-driven, independent of the main power supply line.

Advantageously, also inside the carrying case or in any case forming part of the kit, there may also be a support for keeping the main body, and hence the analysis chamber, vertical during analysis of the product.

In a preferred embodiment, the carrying case is connectable to the machine 17; purely by way of example, the connection may be made through a serial cable or it may be wireless.

In this configuration, the electronic controller unit 10 acts in conjunction with the machine 17 for performing tests on the product mix present in the machine 17 itself.

Advantageously, the results of the tests can be saved to a suitable memory register installed in the machine 17 or in the carrying case.

Depending on the results of these tests (obviously indicating the bacteria concentration in the product) the electronic controller unit 10 can send to the machine 17 corresponding control signals, so as to make the machine 17 perform cleaning and pasteurizing operations.

The test activities briefly described above may conveniently be considered as implementing a food safety monitoring system of the type known as HACCP (Hazard Analysis and Critical Control Points).

The invention achieves the set aims and brings significant advantages. The device described allows accurate and reliable measurements to be obtained. Moreover, the possibility of detecting the bacterial charge in the food product mixes directly on the machine all the time and at all stages of machine operation allows the safety and hygiene of the food prepared to be guaranteed.

Lastly, the portable kit allows analysis even of products made with machines which are not equipped with the device according to the invention.

The invention described above is susceptible of industrial application and may be modified and adapted in several ways without thereby departing from the scope of the inventive concept. Moreover, all details of the invention may be substituted by technically equivalent elements.

What is claimed is:

1. A device for detecting a bacterial charge in a liquid or semi-liquid food product, comprising:
    a main containment body,
    an analysis chamber, located inside the containment body, to contain a certain quantity of a liquid or semi-liquid food product to be examined,
    at least one heating device to heat the product inside the analysis chamber,
    at least one temperature sensor to monitor a temperature of the product inside the analysis chamber,
    a sensor system to detect an impedance of the product inside the analysis chamber for determining a bacterial charge of the product,
    wherein the analysis chamber has an elongate shape and extends along a principal axis that is substantially vertical, a first plane extending along the principal axis dividing the analysis chamber into a first side positioned on a first side of the first plane and a second side positioned on a second side of the first plane to be opposite the first side;
    wherein the at least one heating device is symmetrical about a second plane normal to the principal axis, and the at least one heating device is constructed and arranged to be positioned entirely on the first side, thereby making the first side a warm side of the analysis chamber, the second side opposite the first side having an exterior thermally acted upon by the containment body having a temperature lower than a temperature of the at least one heating device to make the second side a cool side of the analysis chamber having a temperature lower than a temperature of the warm first side;
    wherein the analysis chamber is contained inside a cartridge removably associated with the main containment body;
    the main containment body including a housing into which the cartridge containing the chamber is inserted;
    the sensor system including electrodes fixed to the cartridge to be movable with the cartridge, the electrodes positioned entirely on the second side of the analysis chamber away from the at least one heating element;
    the main containment body including sliding electrical contacts for electrically contacting contact portions of the electrodes of the sensor system fixed to the cartridge when the cartridge is inserted in the housing.

2. The device according to claim 1, wherein the principal axis of the analysis chamber is vertical.

3. The device according to claim 1, wherein the analysis chamber has a circular cross section and has at least one openable end.

4. The device according to claim 1, wherein a ratio between height and base diameter of the analysis chamber with circular cross section is greater than or equal to 2.

5. The device according to claim 1, wherein the sensor system electrodes include portions facing each other inside the analysis chamber; the facing portions of the electrodes promoting circulation of electric current within the product to be analyzed.

6. The device according to claim 1, wherein the analysis chamber is contained within a disposable cartridge and has at least one openable end.

7. The device according to claim 6, wherein the sensor system electrodes are embedded in a wall of the cartridge and include portions facing both an inside and an outside of the analysis chamber, the portions facing the outside of the analysis chamber constituting the contact portions.

8. The device according to claim 1, comprising an electronic controller unit connected electrically to the main containment body.

9. The device according to claim 8, wherein the electronic controller unit controls and coordinates the temperature sensor, the sensor system and the at least one heating device.

10. The device according to claim 9, wherein the electronic controller unit receives temperature values as input from the temperature sensor and operates on the at least one heating device to control and vary the temperature inside the analysis chamber.

11. The device according to claim 9, wherein the electronic controller unit is operatively connected to the sensor system through the sensor system electrodes, for measuring an impedance from which capacitance can be derived to determine the bacterial charge.

12. The device according to claim 8, wherein the electronic controller unit comprises a temperature regulator connected to the temperature sensor, and an electronic card connected to the sensor system, to the at least one heating device and to the temperature regulator.

13. The device according to claim 8, comprising a control panel for controlling and interacting with the electronic controller unit.

14. A machine for producing and dispensing liquid or semi-liquid food products, comprising a food product container, a food product feeding and treating circuit, a dispensing mechanism located at an outlet end of the feeding and treating circuit, and a device for detecting the bacterial charge according to claim 1.

15. A portable kit for detecting the bacterial charge in a liquid or semi-liquid food product, comprising a transportable case and, housed in said case, a device for detecting the bacterial charge according to claim 1.

16. The kit according to claim 15, comprising a power supply unit independent of the mains and including a battery.

17. The kit according to claim 15, comprising a support for the device for detecting the bacterial charge to keep the main containment body of the device in the vertical position when in use.

18. The kit according to claim 15 wherein the device for detecting the bacterial charge comprises an electronic controller unit connectable to a machine for producing and dispensing liquid or semi-liquid food products, said electronic controller unit being configured to perform one or more steps of detecting the bacterial charge in a food product contained in said machine.

19. The kit according to claim 18, wherein the electronic controller unit is also configured to send to said machine control signals for activating at least one of cleaning and pasteurizing operations according to the detection of bacterial charge.

20. The device according to claim 1, wherein an energy input for the at least one heating device is near a center of the symmetrical arrangement.

21. A method for detecting a bacterial charge in a liquid or semi-liquid food product, comprising:
    providing a main containment body,
    providing an analysis chamber, located inside the containment body, to contain a certain quantity of a liquid or semi-liquid food product to be examined, providing at least one heating device to heat the product inside the analysis chamber, providing at least one temperature sensor to monitor a temperature of the product inside the analysis chamber, providing a sensor system to detect an impedance of the product inside the analysis chamber for determining a bacterial charge of the product, providing that the analysis chamber has an elongate shape and extends along a principal axis that is substantially vertical, a first plane extending along the principal axis dividing the analysis chamber into a first side positioned on a first side of the first plane and a second side positioned on a second side of the first plane to be opposite the first side;

providing that the at least one heating device is symmetrical about a second plane normal to the principal axis, heating the first side with the at least one heating device to make the first side a warm side of the analysis chamber, maintaining the second side at a temperature lower than a temperature of the at least one heating device to make the second side a cool side of the analysis chamber having a temperature lower than a temperature of the warm first side, thereby creating a recirculating flow in the product to be examined that is contained within the analysis chamber whereby the flow ascends on the first side and descends on the second side and whereby the flow on the second side is stable and constant with a lower fluid speed than the flow of the first side;

providing that the analysis chamber is contained inside a cartridge removably associated with the main containment body;

providing that the main containment body includes a housing into which the cartridge containing the chamber is inserted;

providing that the sensor system includes electrodes fixed to the cartridge to be movable with the cartridge and a gap between the electrodes where the impedance of the product is measured;

positioning the electrodes entirely on the second side of the analysis chamber away from the at least one heating element to position the gap in the stable and constant lower fluid speed of the second side, as compared to the higher fluid speed of the first side of the analysis chamber adjacent the at least one heating element;

providing that the main containment body includes sliding electrical contacts for electrically contacting contact portions of the electrodes of the sensor system fixed to the cartridge when the cartridge is inserted in the housing.

22. The method of claim 21, and further comprising providing that the lower fluid speed at steady state in which the gap is positioned is approximately one third of the higher fluid speed at steady state of the first side.

23. The method of claim 21, and further comprising providing that an average of the lower fluid speed in which the gap is positioned is between 0.05 and 0.09 m/s.

* * * * *